US012693435B2

(12) United States Patent
Nukanobu et al.

(10) Patent No.: US 12,693,435 B2
(45) Date of Patent: Jul. 28, 2026

(54) RADIATION IMAGING SYSTEM, IMAGING CONTROL DEVICE, AND STORAGE MEDIUM

(71) Applicant: Konica Minolta, Inc., Tokyo (JP)

(72) Inventors: Takeshi Nukanobu, Hachioji (JP); Keisuke Koeda, Higashimurayama (JP); Mao Eguchi, Kokubunji (JP); Atsushi Taneda, Koganei (JP); Hiroaki Nakano, Sagamihara (JP)

(73) Assignee: KONICA MINOLTA, INC., Tokyo (JP)

( * ) Notice: Subject to any disclaimer, the term of this patent is extended or adjusted under 35 U.S.C. 154(b) by 157 days.

(21) Appl. No.: 18/151,529

(22) Filed: Jan. 9, 2023

(65) Prior Publication Data

US 2023/0161055 A1     May 25, 2023

Related U.S. Application Data

(63) Continuation of application No. 17/108,500, filed on Dec. 1, 2020, now abandoned.

(30) Foreign Application Priority Data

Dec. 3, 2019     (JP) ................................. 2019-218444

(51) Int. Cl.
  *G01T 1/163*          (2006.01)
  *A61B 6/00*          (2006.01)
      (Continued)
(52) U.S. Cl.
  CPC ................ *G01T 1/175* (2013.01); *A61B 6/54* (2013.01); *H04N 23/30* (2023.01)
(58) Field of Classification Search
  None
  See application file for complete search history.

(56) References Cited

U.S. PATENT DOCUMENTS 9,146,326 B2     9/2015   Kuwabara et al.
9,322,928 B2     4/2016   Iwakiri et al.
        (Continued)

FOREIGN PATENT DOCUMENTS

JP        2011152406 A     8/2011
JP        2012161530 A     8/2012
        (Continued)

OTHER PUBLICATIONS

JPO Notice of Reasons of Refusal for corresponding JP Application No. 2023-085840; Mailing Date, Dec. 12, 2023.
        (Continued)

*Primary Examiner* — Hoon K Song
(74) *Attorney, Agent, or Firm* — CANTOR COLBURN LLP

(57)          ABSTRACT

A radiation imaging system including: a radiation generator that includes a radiation source generating a radiation pulse by receiving a tube current of a preset amount; a radiation detector that includes a plurality of charge accumulators which accumulate and release electric charges to be read out as signal values according to received radiation and that generates a dynamic image formed of a plurality of frames; and a hardware processor. The hardware processor sets an amount of the tube current and a length of an accumulation time for which the charge accumulators are allowed to accumulate the electric charges, calculates such a proper range of the tube current that start and end of generation of one radiation pulse by the radiation generator are within one accumulation time to perform an imaging with the accumulation time, and regulates setting of a value out of the proper range.

7 Claims, 13 Drawing Sheets

| No. | ACCUMULATION TIME | FRAME RATE/ PIXEL | IRRADITAION TIME | TUBE CURRENT | TUBE VOLTAGE | MAXIMUM IMAGING NUMBER | mAs/f | MAXIMUM ONE IMAGING | MAXIMUM IMAGING TIME |
|---|---|---|---|---|---|---|---|---|---|
| 1 | 10ms | 15fps /400μ | 1 ~ 8ms | 80 ~ 250mA | 50 ~ 125kV | 300 | 0.08 ~ 2mAs/f | 600mAs | 20s |
| 2 | 70ms | 7.5fps /400μ | 1 ~ 8ms | 32 ~ 250mA | 50 ~ 125kV | 150 | 0.03 ~ 2mAs/f | 300mAs | 20s |
| 3 | 200ms | 3.75fps /400μ | 1 ~ 8ms | 20 ~ 250mA | 50 ~ 125kV | 75 | 0.02 ~ 2mAs/f | 150mAs | 20s |

(51) Int. Cl.
    *G01T 1/175*       (2006.01)
    *H04N 23/30*      (2023.01)

(56)          References Cited

U.S. PATENT DOCUMENTS

| | | | |
|---|---|---|---|
| 2011/0317054 A1 | 12/2011 | Kameshima et al. | |
| 2012/0274855 A1* | 11/2012 | Aokage ................ | H04N 25/618 |
| | | | 348/E5.077 |
| 2014/0110595 A1* | 4/2014 | Iwakiri ................ | A61B 6/4233 |
| | | | 250/394 |
| 2015/0071414 A1* | 3/2015 | Oda ..................... | A61B 6/4266 |
| | | | 378/207 |
| 2021/0011176 A1 | 1/2021 | Ishinari et al. | |
| 2022/0035054 A1 | 2/2022 | Ohguri | |

FOREIGN PATENT DOCUMENTS

| | | | |
|---|---|---|---|
| JP | 2019166107 A | 10/2019 | |
| WO | 2013015350 A1 | 1/2013 | |

OTHER PUBLICATIONS

USPTO Non-Final Office Action for corresponding U.S. Appl. No. 17/108,500; dated Aug. 11, 2022.
JPO Notice of Reasons for Refusal for corresponding JP Application No. 2019-218444; Mailing Date, Mar. 28, 2023.

\* cited by examiner

| No. | ACCUMULATION TIME | FRAME RATE/ PIXEL | IRRADITAION TIME | TUBE CURRENT | TUBE VOLTAGE | MAXIMUM IMAGING NUMBER | mAs/f | MAXIMUM ONE IMAGING | MAXIMUM IMAGING TIME |
|---|---|---|---|---|---|---|---|---|---|
| 1 | 10ms | 15fps /400μ | 1 ～ 8ms | 80 ～ 250mA | 50 ～ 125kV | 300 | 0.08 ～ 2mAs/f | 600mAs | 20s |
| 2 | 70ms | 7.5fps /400μ | 1 ～ 8ms | 32 ～ 250mA | 50 ～ 125kV | 150 | 0.03 ～ 2mAs/f | 300mAs | 20s |
| 3 | 200ms | 3.75fps /400μ | 1 ～ 8ms | 20 ～ 250mA | 50 ～ 125kV | 75 | 0.02 ～ 2mAs/f | 150mAs | 20s |

FIG. 9

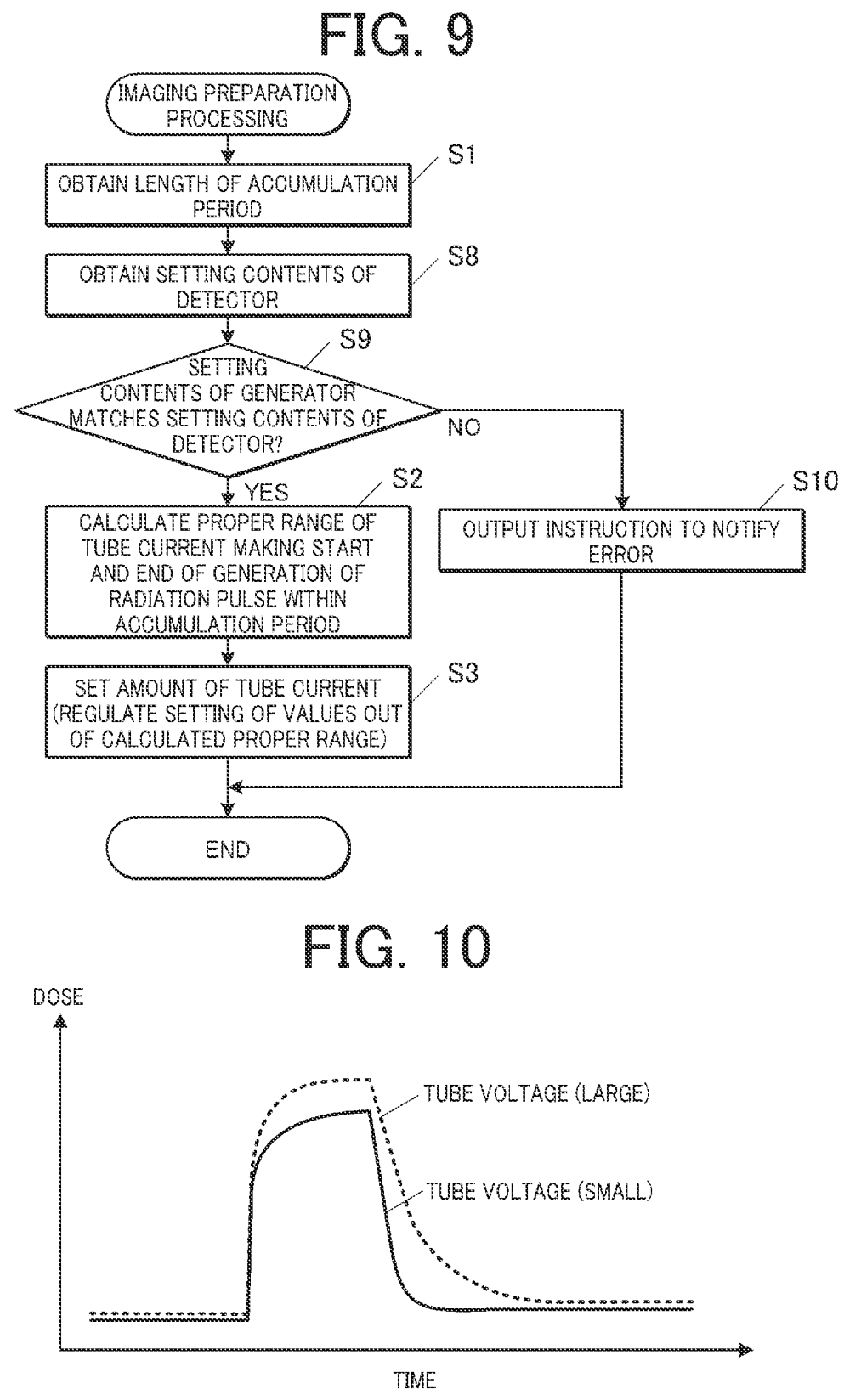

IMAGING PREPARATION
PROCESSING

OBTAIN LENGTH OF ACCUMULATION
PERIOD — S1

OBTAIN SETTING CONTENTS OF
DETECTOR — S8

SETTING
CONTENTS OF GENERATOR
MATCHES SETTING CONTENTS OF
DETECTOR? — S9

NO

YES

CALCULATE PROPER RANGE OF
TUBE CURRENT MAKING START
AND END OF GENERATION OF
RADIATION PULSE WITHIN
ACCUMULATION PERIOD — S2

OUTPUT INSTRUCTION TO NOTIFY
ERROR — S10

SET AMOUNT OF TUBE CURRENT
(REGULATE SETTING OF VALUES OUT
OF CALCULATED PROPER RANGE) — S3

END

FIG. 10

DOSE

TUBE VOLTAGE (LARGE)

TUBE VOLTAGE (SMALL)

TIME

FIG. 11

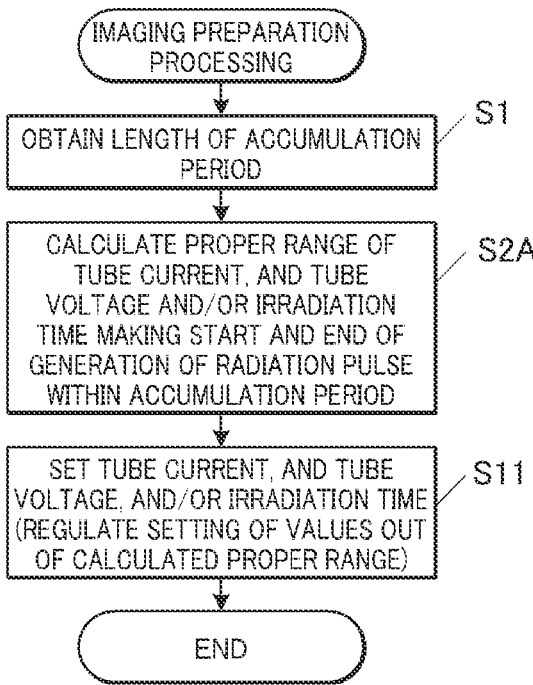

IMAGING PREPARATION PROCESSING

↓

OBTAIN LENGTH OF ACCUMULATION PERIOD — S1

↓

CALCULATE PROPER RANGE OF TUBE CURRENT, AND TUBE VOLTAGE AND/OR IRRADIATION TIME MAKING START AND END OF GENERATION OF RADIATION PULSE WITHIN ACCUMULATION PERIOD — S2A

↓

SET TUBE CURRENT, AND TUBE VOLTAGE, AND/OR IRRADIATION TIME (REGULATE SETTING OF VALUES OUT OF CALCULATED PROPER RANGE) — S11

↓

END

FIG. 12

| No. | ACCUMULATION TIME | FRAME RATE/ PIXEL | IRRADITAION TIME | TUBE CURRENT | TUBE VOLTAGE | MAXIMUM IMAGING NUMBER | mAs/f | MAXIMUM ONE IMAGING | MAXIMUM IMAGING TIME |
|---|---|---|---|---|---|---|---|---|---|
| 1 | 10ms | 15fps /400 μ | 1 ~ 8ms | 80 ~ 250mA | 50 ~ 125kV | 300 | 0.08 ~ 2mAs/f | 600mAs | 20s |
| 2 | 70ms | 7.5fps /400 μ | 1 ~ 16ms | 32 ~ 250mA | 50 ~ 135kV | 300 | 0.03 ~ 4mAs/f | 1200mAs | 40s |
| 3 | 200ms | 3.75fps /400 μ | 1 ~ 32ms | 20 ~ 250mA | 50 ~ 150kV | 300 | 0.02 ~ 8mAs/f | 2400mAs | 80s |

FIG. 13

| No. | ACCUMULATION TIME | FRAME RATE/ PIXEL | IRRADITAION TIME | TUBE CURRENT | TUBE VOLTAGE | MAXIMUM IMAGING NUMBER | mAs/f | MAXIMUM ONE IMAGING | MAXIMUM IMAGING TIME |
|---|---|---|---|---|---|---|---|---|---|
| 1 | 10ms | 15fps /400μ | 1 ~ 8ms | 80 ~ 250mA | 50 ~ 125kV | 300 | 0.08 ~ 2mAs/f | 600mAs | 20s |
| 2 | 70ms | 7.5fps /400μ | 1 ~ 16ms | 32 ~ 250mA | 50 ~ 135kV | 150 | 0.03 ~ 4mAs/f | 600mAs | 20s |
| 3 | 200ms | 3.75fps /400μ | 1 ~ 32ms | 20 ~ 250mA | 50 ~ 150kV | 75 | 0.02 ~ 8mAs/f | 600mAs | 20s |

FIG. 14

| No. | ACCUMULATION TIME | FRAME RATE/ PIXEL | IRRADITAION TIME | TUBE CURRENT | TUBE VOLTAGE | MAXIMUM IMAGING NUMBER | mAs/f | MAXIMUM ONE IMAGING | MAXIMUM IMAGING TIME |
|---|---|---|---|---|---|---|---|---|---|
| 1 | 10ms | 15fps /400μ | 1 ~ 8ms | 80 ~ 250mA | 50 ~ 125kV | 300 | 0.08 ~ 2mAs/f | 600mAs | 20s |
| 2 | 70ms | 7.5fps /400μ | 1 ~ 16ms | 32 ~ 250mA | 50 ~ 135kV | 150 | 0.03 ~ 4mAs/f | 600mAs | 20s |
| 3 | 200ms | 3.75fps /400μ | 1 ~ 32ms | 20 ~ 250mA | 50 ~ 150kV | 75 | 0.02 ~ 8mAs/f | 600mAs | 20s |
| 4 | 70ms | 7.5fps /400μ | 1 ~ 8ms | 32 ~ 250mA | 50 ~ 135kV | 300 | 0.03 ~ 2mAs/f | 600mAs | 40s |
| 5 | 200ms | 3.75fps /400μ | 1 ~ 8ms | 20 ~ 250mA | 50 ~ 150kV | 300 | 0.02 ~ 2mAs/f | 600mAs | 80s |

FIG. 15

| No. | ACCUMULATION TIME | FRAME RATE/ PIXEL | IRRADITAION TIME | TUBE CURRENT | TUBE VOLTAGE | MAXIMUM IMAGING NUMBER | mAs/f | MAXIMUM ONE IMAGING | MAXIMUM IMAGING TIME |
|-----|-----|-----|-----|-----|-----|-----|-----|-----|-----|
| 1 | 10ms | 15fps /400 $\mu$ | 1 ~ 8ms | 80 ~ 250mA | 50 ~ 125kV | 300 | 0.08 ~ 2mAs/f | 600mAs | 20s |
| 2 | 70ms | 7.5fps /400 $\mu$ | 1 ~ 16ms | 32 ~ 250mA | 50 ~ 135kV | 150 | 0.03 ~ 4mAs/f | 600mAs | 20s |
| 3 | 200ms | 3.75fps /400 $\mu$ | 1 ~ 32ms | 20 ~ 250mA | 50 ~ 150kV | 75 | 0.02 ~ 8mAs/f | 600mAs | 20s |
| 4 | 70ms | 7.5fps /400 $\mu$ | 1 ~ 8ms | 32 ~ 250mA | 50 ~ 135kV | 300 | 0.03 ~ 2mAs/f | 600mAs | 40s |
| 5 | 200ms | 3.75fps /400 $\mu$ | 1 ~ 8ms | 20 ~ 250mA | 50 ~ 150kV | 300 | 0.02 ~ 2mAs/f | 600mAs | 80s |
| 6 | 40ms | 6fps /200 $\mu$ | 1 ~ 12ms | 40 ~ 250mA | 50 ~ 130kV | 200 | 0.04 ~ 3mAs/f | 600mAs | 33s |

FIG. 17

|  | FRAME 1 | FRAME 2 | FRAME 3 |
|---|---|---|---|
| SUBJECT | | | |
| LAG IMAGE | NONE | | |
| OBTAINED IMAGE | | | |

RADIATION IMAGING SYSTEM, IMAGING CONTROL DEVICE, AND STORAGE MEDIUM

CROSS-REFERENCE TO RELATED APPLICATIONS

The present application is a continuation application of U.S. patent application Ser. No. 17/108,500, filed on Dec. 1, 2020, the entire contents of which are incorporated herein by reference. The Ser. No. 17/108,500 application claimed the benefit of the date of the earlier filed Japanese Patent Application No. 2019-218444 filed on Dec. 3, 2019, priority to which is also claimed herein, and the contents of which are also incorporated by reference herein.

BACKGROUND

Technological Field

The present invention relates to a radiation imaging system, an imaging control device, and a storage medium.

Description of the Related Art

The sites of interest to be diagnosed by a person who performs diagnosis have different movement speeds according to the positions of the sites and the ways of movement. Even for a same site of interest, the image quality required for a radiation image used in the diagnosis is different according to the purpose of diagnosis (for example, diagnosis of movement in breathing or diagnosis of movement of bloodstream, as for a chest).

Thus, in dynamic imaging of generating a dynamic image formed of a plurality of frames by using a radiation generator which repeatedly generates radiation pulses and a radiation detector which repeatedly generates radiation images according to the received radiation, imaging has been conventionally performed by switching to a desired (according to the site of interest and the purpose of diagnosis) frame rate from among a plurality of different frame rates.

In order to obtain a dynamic image which has no problem in image quality, it is necessary to generate radiation pulses while the radiation detector can accumulate electric charges (during accumulation time).

Thus, as described in JP 2012-161530 A, for example, there has been conventionally performed a control in a radiation image capturing system including a radiation irradiation device and a radiation image capturing device, the control making the radiation emitted by pulse irradiation from the radiation irradiation device to the radiation image capturing device with a rate of irradiation period to each frame period for capturing each frame image according to the frame rate of fluoroscopic imaging within a range of 12.5% to 80%, while causing the radiation image capturing device to perform capturing of the radiation image in synchronization with the pulse irradiation.

SUMMARY

The radiation pulse generated by the radiation generator does not reach a predetermined dose at the same time as the start of generating the radiation pulse, and the dose does not reach zero at the same time as the end of generating the radiation pulse. That is, there is known that, when the change over time of the dose of radiation pulse is shown by a graph, the graph does not draw a rectangle but draws a nearly trapezoid with the rising portion and the falling portion which are inclined.

As shown in FIG. 1, the inclination of each of the rising and falling portions (especially, falling portion) is steep when the tube current is large, but the inclination is more gradual as the tube current is smaller.

However, the conventional radiation imaging system as described in above JP 2012-161530 A controls the radiation generator and the radiation detector such that the irradiation time of the radiation pulse is within the accumulation time. The irradiation time is generally the time after the radiation pulse reaches a predetermined dose until the radiation pulse returns to the same dose.

That is, in the conventional radiation imaging system, the inclination property of the radiation pulse as mentioned above is not considered. Thus, when the dynamic imaging is performed by setting the tube current to be small, by attempting to make the irradiation time of the radiation pulse within the accumulation time, the timing when the generation of radiation pulse starts and the timing when the generation of radiation pulse ends go out of the accumulation time, and the dynamic image influenced by this situation is possibly generated.

Such a problem is more remarkable as the frame rate is higher.

The present invention has been made in consideration of the above matters, and an object of the present invention is to enable generating a dynamic image without problem in image quality even when the tube current is small, in dynamic imaging using a radiation generator and a radiation detector, the radiation generator including a radiation source that generates radiation pulse by receiving supply of a preset amount of the tube current, and the radiation detector including a plurality of charge accumulators that accumulate and release electric charges to be read out as signal values according to the received radiation and generating a dynamic image formed of a plurality of frames.

To achieve at least one of the abovementioned objects, according to an aspect of the present invention, a radiation imaging system reflecting one aspect of the present invention is a radiation imaging system including: a radiation generator that includes a radiation source which generates a radiation pulse by receiving supply of a tube current of a preset amount; a radiation detector that includes a plurality of charge accumulators which accumulate and release electric charges to be read out as signal values according to received radiation and that generates a dynamic image formed of a plurality of frames; and a hardware processor that: sets an amount of the tube current and a length of an accumulation time for which the charge accumulators are allowed to accumulate the electric charges; calculates such a proper range of the tube current that start and end of generation of one of the radiation pulse by the radiation generator are within one of the set accumulation time to perform an imaging with the set accumulation time; and regulates setting of a value out of the calculated proper range.

To achieve at least one of the abovementioned objects, according to another aspect of the present invention, an imaging control device reflecting one aspect of the present invention is an imaging control device that controls a radiation generator and a radiation detector, the radiation generator including a radiation source which generates a radiation pulse by receiving supply of a tube current of a preset amount, the radiation detector including a plurality of charge accumulators which accumulate and release electric charges to be read out as signal values according to received radiation and generating a dynamic image formed of a plurality of frames, and the imaging control device comprising a hardware processor that: sets an amount of the tube current; calculates such a proper range of the tube current that start and end of generation of one of the radiation pulse by the radiation generator are within one of an accumulation time which is set in advance to perform an imaging with the set accumulation time; and regulates setting of a value out of the calculated proper range.

To achieve at least one of the abovementioned objects, according to another aspect of the present invention, a storage medium reflecting one aspect of the present invention is a non-transitory storage medium storing a computer readable program for a computer in an imaging control device that controls a radiation generator and a radiation detector, the radiation generator including a radiation source which generates a radiation pulse by receiving supply of a tube current of a preset amount, the radiation detector including a plurality of charge accumulators which accumulate and release electric charges to be read out as signal values according to received radiation and generating a dynamic image formed of a plurality of frames, and the program causing the computer to perform: setting an amount of the tube current; calculating such a proper range of the tube current that start and end of generation of one of the radiation pulse by the radiation generator are within one of an accumulation time which is set in advance to perform an imaging with the set accumulation time; and regulating setting of a value out of the calculated proper range.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 9 is a flowchart showing the flow of other imaging preparation processing executed by the imaging control device in FIG. 5;

FIG. 10 is a graph showing the change over time of the radiation pulse;

FIG. 11 is a flowchart showing the flow of other imaging preparation processing executed by the imaging control device in FIG. 5;

FIG. 12 is a table showing another setting example of the radiation irradiation condition and the imaging condition for each accumulation time;

FIG. 13 is a table showing another setting example of the radiation irradiation condition and the imaging condition for each accumulation time;

FIG. 14 is a table showing another setting example of the radiation irradiation condition and the imaging condition for each accumulation time;

FIG. 15 is a table showing another setting example of the radiation irradiation condition and the imaging condition for each accumulation time;

FIG. 17 is a view showing a manner in which the lag is generated; and

DETAILED DESCRIPTION OF EMBODIMENTS

Hereinafter, one or more embodiments of the present invention will be described with reference to the drawings. However, the scope of the invention is not limited to the disclosed embodiments or the illustrated examples.
<1. Configuration of Radiation Imaging System>

Figure 2:
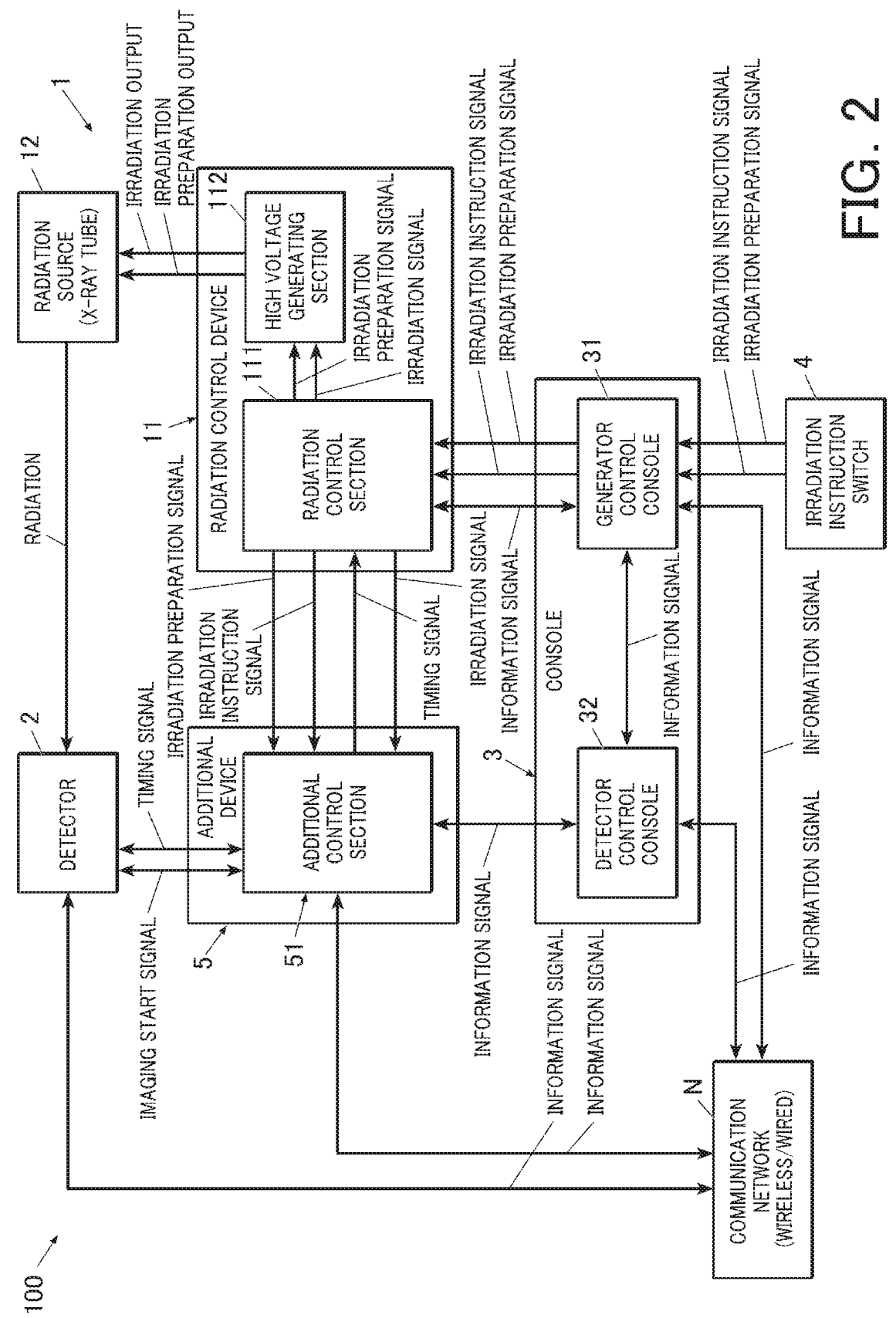
FIG. 2 is a block diagram showing a radiation imaging system according to an embodiment of the present invention.
Figure 3:
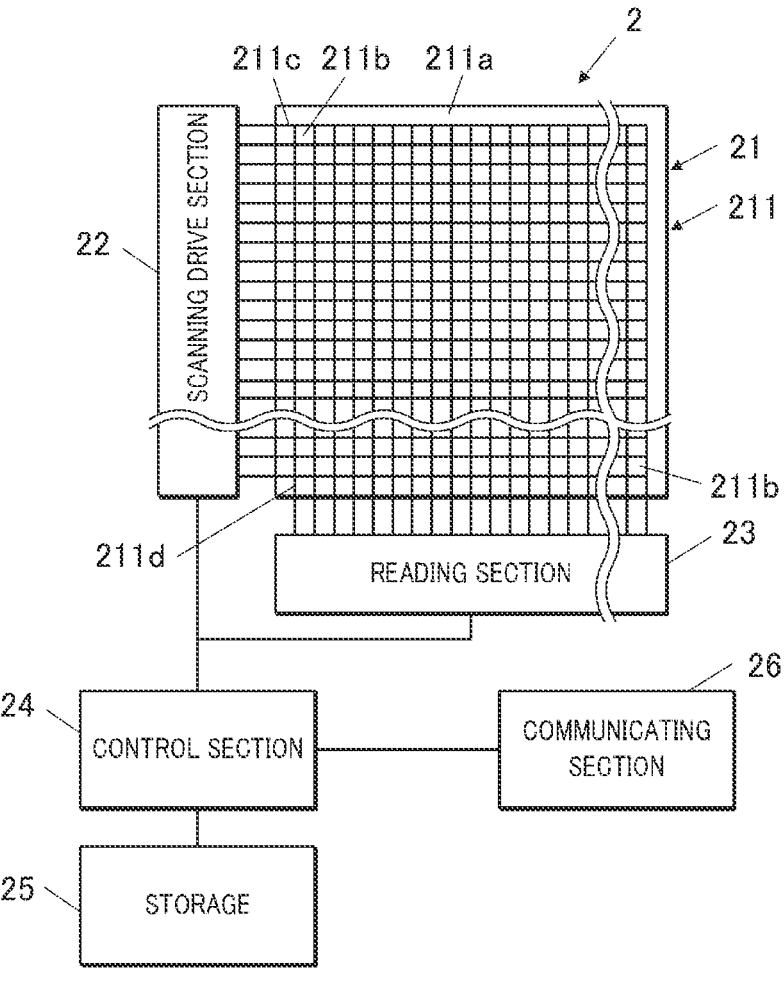
FIG. 3 is a block diagram showing a radiation detector which is included in the radiation imaging system in FIG. 2.
Figure 4:
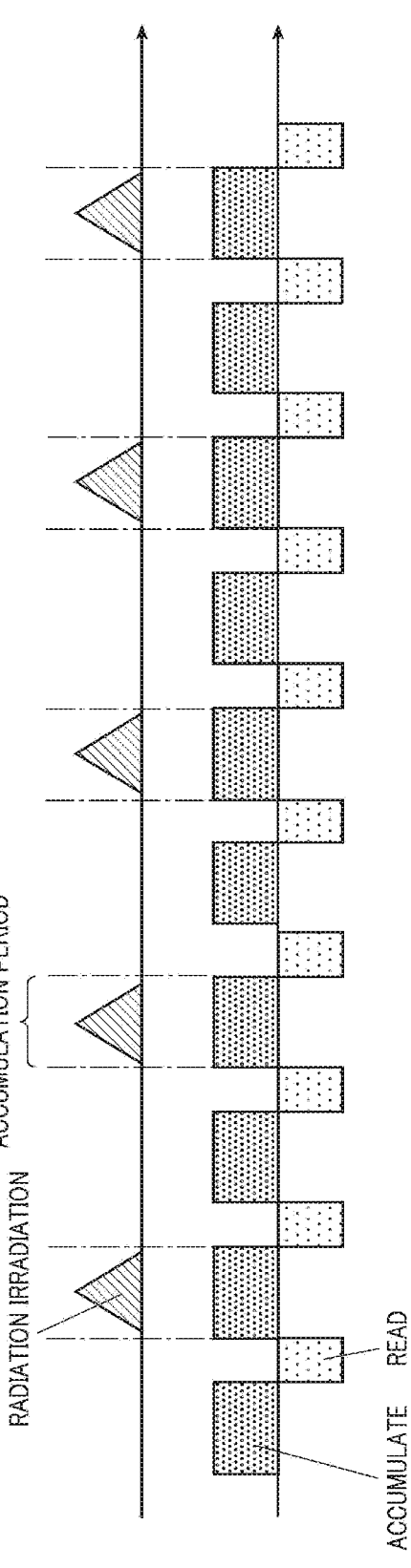
FIG. 4 is a view showing the operation of the radiation imaging system in FIG. 2 at the time of dynamic imaging.
Figure 5:
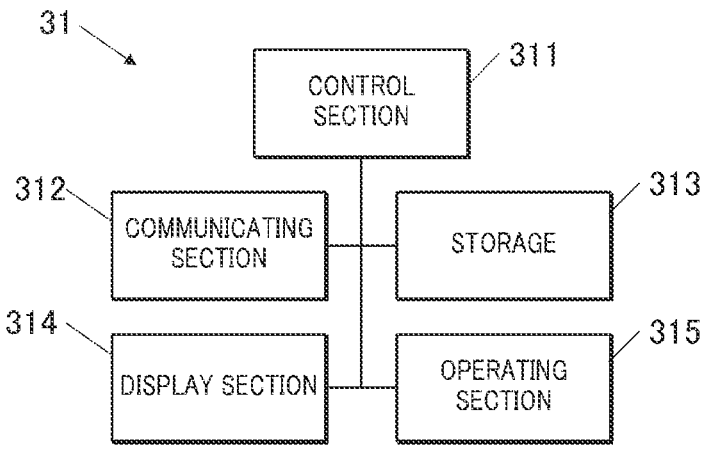
FIG. 5 is a block diagram showing an imaging control device (generator control console) which is included in the radiation imaging system in FIG. 2.

The schematic configuration of a radiation imaging system according to the present embodiment (hereinafter, referred to as a system 100) will be first described. FIG. 2 is a block diagram showing the system 100, FIG. 3 is a block diagram of a radiation detector (hereinafter, referred to as a detector 2) which is included in the system 100, FIG. 4 is a timing chart showing the operation when imaging (hereinafter, referred to as dynamic imaging) of a dynamic image is performed by using the system 100, and FIG. 5 is a block diagram of a generator control console 31 which is included in the system 100.

As shown in FIG. 2, the system 100 includes a radiation generator (hereinafter, referred to as a generator 1), the radiation detector (hereinafter, referred to as detector 2), and a console 3, for example.

The system 100 according to the present embodiment further includes an irradiation instruction switch (hereinafter, referred to as a switch 4), and an additional device 5.

The system 100 may be communicable to Radiology Information System (RIS) and Picture Archiving and Communication System (PACS) via a communication network N (Local Area Network (LAN), Wide Area Network (WAN), internet or the like).
[1-1. Radiation Generator]

The generator 1 includes a radiation control device 11 and a radiation source 12.

The radiation control device 11 includes a radiation control section 111 and a high voltage generating section 112.

The radiation control section 111 and the high voltage generating section 112 are electrically connected to each other.

The radiation control section 111 controls radiation irradiation.

To be specific, in response to turning on of an irradiation preparation signal which is input from the generator control console 31, the radiation control section 111 turns on the irradiation preparation signals which are output to the high voltage generating section 112 and the additional device 5.

In response to turning on of the irradiation instruction signal which is input from the generator control console 31 and instructs radiation irradiation, the radiation control section 111 turns on the irradiation instruction signal output to the additional device 5, and transmits the irradiation signal corresponding to the radiation irradiation condition, which was set by the generator control console 31, to the high voltage generating section 112.

In response to turning on of the irradiation preparation signal which is input from the radiation control section 111, the high voltage generating section 112 outputs the irradiation preparation output to the radiation source 12.

In response to receiving of the irradiation signal from the radiation control section 111, the high voltage generating section 112 applies a tube voltage which was set in advance as the irradiation output to the radiation source 12, and supplies a preset amount of tube current to the radiation source 12.

The radiation source 12 (tube) generates radiation (for example, X-ray) by receiving the supply of the preset amount of tube current from the high voltage generating section 112.

The generator 1 which is configured in such a way generates radiation corresponding to the imaging condition and the radiation irradiation condition which were set in advance, according to the signal input from the generator control console 31 (from an after-mentioned irradiation instruction switch 4).

[1-2. Radiation Detector]

As shown in FIG. 3, the detector 2 includes a sensor section 21, a scanning drive section 22, a reading section 23, a control section 24, a storage 25 and a communicating section 26.

The above sections 21 to 26 are electrically connected to each other.

The sensor section 21 includes a scintillator not shown in the drawings and a photoelectric conversion panel 211.

The scintillator is formed in a flat plate shape with a columnar crystal of CsI, for example.

By receiving radiation, the scintillator emits electromagnetic waves (for example, visible light) having a longer wavelength than the wavelength of radiation, with the intensity corresponding to the dose of the received radiation (mAs).

The scintillator is arranged to spread in parallel with the radiation incidence plane of a housing not shown in the drawings.

The photoelectric conversion panel 211 is arranged to spread in parallel to the scintillator, on the opposite side to the face of the scintillator facing the radiation incidence plane of the housing.

The photoelectric conversion panel 211 includes a substrate 211*a* and a plurality of charge accumulators 211*b*.

The plurality of charge accumulators 211*b* are arranged two dimensionally (for example, in a matrix) to correspond to respective pixels in the radiation image on the surface of the substrate facing the scintillator.

Each of the charge accumulators 211*b* includes a semiconductor element which generates an electric charge of an amount corresponding to the intensity of electromagnetic wave generated by the scintillator, and a switching element which is provided between the semiconductor element and the wiring connected to the reading section 23.

A bias voltage is applied to each semiconductor element from a power supply circuit not shown in the drawings.

By switching on/off of the switching element, each of the charge accumulators 211*b* accumulates the electric charge to be read out as a signal value according to the received radiation and releases the electric charge.

By applying an on voltage or an off voltage to each of the scanning lines 211*c* of the sensor section 21, the scanning drive section 22 can switch each of the switching elements to an on state or an off state.

The reading section 23 reads out, as the signal value, the amount of electric charges which flow from the charge accumulator 211*b* via each signal line 211*d* of the sensor section 21.

The reading section 23 may perform binning when the reading section 23 reads out the signal values.

The control section 24 includes a Central Processing Unit (CPU) and a Random Access Memory (RAM) not shown in the drawings.

The CPU reads out various types of processing programs stored in the storage 25 and loads them to the RAM, executes various types of processing in accordance with the processing programs, and thereby integrally controls the operation of each of the sections in the detector 2.

The control section 24 generates image data of a radiation image on the basis of a plurality of signal values which were read out by the reading section 23.

The storage 25 is configured by including an HDD (Hard Disk Drive), a semiconductor memory, or the like, and stores processing programs for executing various types of processing, parameters necessary for executing the processing programs, files and the like.

The storage 25 may be configured to be able to store image data of the radiation image.

The communicating section 26 is able to transmit and receive various signals and various types of data (data of the radiation image, and the like) to and from other devices (for example, console 3) connected via the communication network N.

The detector 2 configured in such a way repeats a series of operations of switching to the accumulating state and switching to the reading state after a preset accumulation time elapses, each time an imaging timing signal is received from the additional device 5.

The "accumulating state" in the embodiment is a state in which the off voltage is applied to each of the switching elements, and the electric charges generated by the semiconductor element are accumulated in the charge accumulators 211*b*.

The "reading state" is a state in which the on voltage is applied to each of the switching elements, the electric charges accumulated in the charge accumulator 211*b* are released, and the reading section 23 reads out the amount of the electric charges which flow in from the charge accumulators 211*b* as signal values.

The detector 2 generates the dynamic image formed of a plurality of frames by repeating the accumulating state and the reading state.

The detector 2 transmits the generated data of the dynamic image to the console 3 as needed.

[1-3. Console]

As shown in FIG. 2, the console 3 includes the generator control console 31 and the detector control console 32.

The generator control console 31 and the detector control console 32 may be integrated as a single device.

(1-3-1. Generator Control Console)

The generator control console 31 in the present embodiment forms an imaging control device.

The details of the generator control console 31 will be described later.

(1-3-2. Detector Control Console)

The detector control console 32 mainly controls the detector 2.

The detector control console 32 is able to set subject information (subject name, sex, age, build, site of interest, and the like) and imaging conditions (accumulation time, frame rate, maximum imaging number, number of binning, and the like) in the detector 2.

The "accumulation time" is a period during which the charge accumulators 211b can accumulate electric charges (until the switching elements of the charge accumulators 211b turn into the on state (conducted state between the semiconductor elements and the reading section 23) after the switching elements turn into the off state (non-conducted state between the semiconductor elements and the reading section 23)).

The "maximum imaging number" is the maximum number of frames which are generated by the detector 2 in a single dynamic imaging.

The detector control console 32 is able to transmit the subject information and the imaging conditions which are set in the detector 2 to the generator control console 31.

The detector control console 32 is also able to set the operation (the period and the number of times as for outputting the irradiation timing signal, and the like) of the additional device 5 in the additional device 5.

The detector control console 32 may change the frame rate which is set according to the set accumulation time, or may not change the frame rate (may maintain a constant frame rate irrespective of the accumulation time).

The detector control console 32 may be able to set the radiation irradiation condition of the generator 1.

The detector control console 32 may receive the radiation irradiation condition and the like from the generator control console 31.

[1-4. Irradiation Instruction Switch]

The switch 4 is for a person who performs the imaging to instruct the radiation irradiation.

The switch 4 in the present embodiment is configured to allow the two-step operation. To be specific, when the switch 4 is pressed to the first step, the switch 4 turns on the irradiation preparation signal to be output to the generator control console 31. When the switch 4 is pressed to the second step, the switch 4 turns on the irradiation instruction signal to be output to the generator control console 31.

Figure 1:
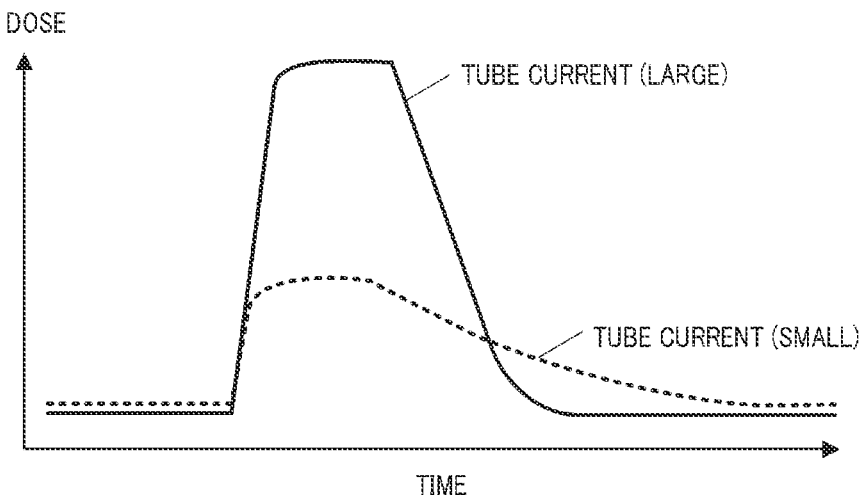
FIG. 1 is a graph showing the change over time of the radiation pulse.

FIG. 1 illustrates a configuration in which the switch 4 is connected to the generator control console 31 and the irradiation preparation signal and the irradiation instruction signal output by the switch 4 are input to the radiation control section 111 via the generator control console 31. However, the switch 4 may be connected to the radiation control section 111 so that the irradiation preparation signal and the irradiation instruction signal are directly input to the radiation control section 111.

[1-5. Additional Device]

The additional device 5 includes an additional control section 51 and a communicating section not shown in the drawings.

The additional control section 51 integrally controls the operations of the sections in the additional device 5 with a CPU, a RAM and the like.

In this configuration, the additional control section 51 reads out various processing programs stored in a storage not shown in the drawings to load them to the RAM, and executes the various types of processing in according with the processing programs.

The communicating section obtains the irradiation preparation signal output by the switch 4 via the radiation control section 111 (generator).

The communicating section obtains the irradiation instruction signal output by the switch 4 via the radiation control section 111 (generator).

The communicating section receives input of an imaging start signal from the detector 2.

The imaging start signal is turned on when the detector 2 comes into a state capable of imaging, and the imaging start signal is turned off when the detector 2 comes into a state not capable of imaging.

The communicating section is able to output the irradiation timing signal to the radiation control section 111.

The additional device 5 configured in such a way is able to repeatedly, at a predetermined period, output the irradiation timing signal that instructs irradiation of radiation to the radiation control section 111 via the communicating section according to the irradiation instruction signal which was obtained from the radiation control section 111 via the communicating section and the imaging start signal which was input from the detector 2 via the communicating section.

The additional device 5 outputs the imaging timing signal instructing the imaging timing of the radiation image from the communicating section to the detector 2 according to the timing to output the irradiation timing signal.

The additional device 5 in the present embodiment repeatedly outputs the imaging timing signal at a same period as the period of the irradiation timing signal.

The additional device 5 repeatedly outputs the irradiation timing signal and the imaging timing signal until the signals are output a predetermined number of times or until a predetermined time has elapsed from the first outputting.

[1-6. Operation]

In the system 100 configured in such a way, the generator 1 and the detector 2 start dynamic imaging when the dynamic imaging is set as one of the imaging conditions in the console 3 and the irradiation instruction switch 13 is pressed by the user.

In the dynamic imaging, as shown in FIG. 4, for example, the detector 2 repeats at a preset frame rate a series of operations of switching to the accumulating state for a preset accumulation time and then switching to the reading state.

Each time the detector 2 switches to the accumulating state (at a preset frame rate), the generator 1 repeatedly emits the radiation pulse of a preset irradiation time to the subject and the detector 2 behind the subject.

The generator 1 and the detector 2 repeat such operations until the detector 2 generates the preset maximum imaging number of frames or until the preset imaging time elapses.

The detector 2 generates a dynamic image formed of a plurality of frames.

<2. Generator Control Console>

Next, the details of the generator control console 31 included in the console 3 of the system 100 will be described.

Figure 6:
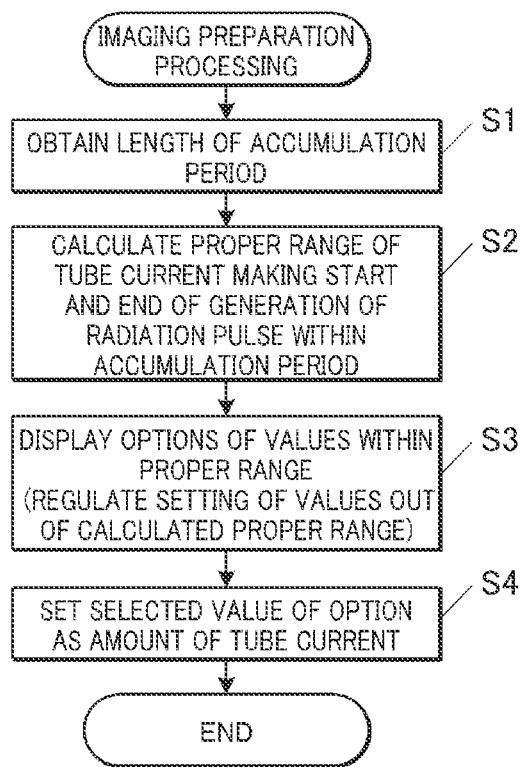
FIG. 6 is a flowchart showing the flow of imaging preparation processing executed by the imaging control device in FIG. 5.
Figures 7, 8:
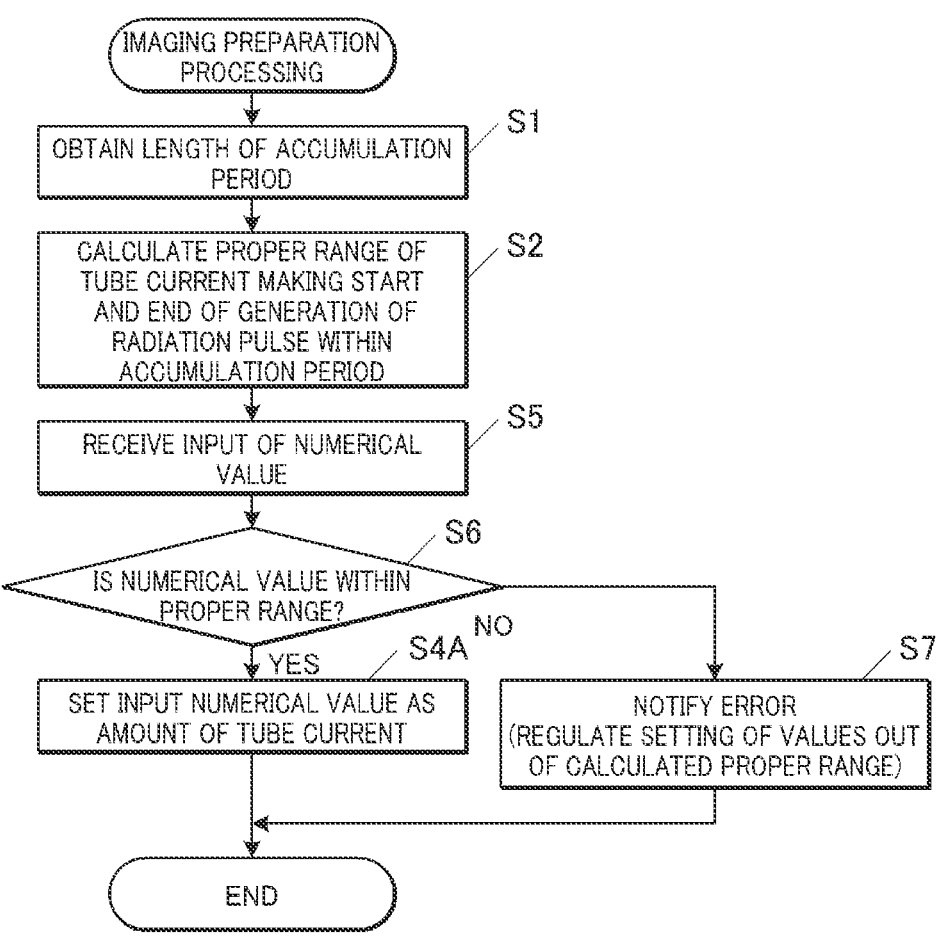
FIG. 7 is a flowchart showing the flow of other imaging preparation processing executed by the imaging control device in FIG. 5.
FIG. 8 is a table showing a setting example of the radiation irradiation condition and the imaging condition for each accumulation time.

FIG. 5 is a block diagram showing the generator control console 31, FIG. 6 is a flowchart showing the flow of imaging preparation processing executed by the control section 311 of the generator control console 31, and FIG. 8 is a table showing a setting example of the radiation irradiation condition and the imaging condition for each accumulation time.

[2-1. Configuration]

As shown in FIG. 5, the generator control console 31 includes a control section 311 (hardware processor), a communicating section 312, a storage 313, a display section 314, and an operating section 315.

The control section 311 is configured by including a CPU, a RAM, and the like.

The CPU of the control section 311 reads out various programs stored in the storage 313 and loads them to the RAM, executes various types of processing in accordance with the loaded programs, and controls the operations of the sections in the generator control console 31 in a centralized manner.

The communicating section 312 is configured by including a wired communication module, a wireless communication module, or the like. The communicating section 312 is able to transmit and receive in a wired manner or wirelessly various signals and various types of data to and from other devices (generator 1, detector 2 and the like) connected via the communication network N.

The storage 313 is configured by including a nonvolatile semiconductor memory, a hard disk, or the like.

The storage 313 stores programs for the control section 311 to execute various types of processing, parameters necessary for executing the programs, and the like.

The storage 313 in the present embodiment is able to save the image data of the radiation image.

The image data may be saved by a saving section which is provided separately from the storage 313.

The display section 314 is configured by including a monitor such as an LCD (Liquid Crystal Display) and a CRT (Cathode Ray Tube). The display section 314 displays various images and various types of information and the like in accordance with instructions of display signals input from the control section 311.

The operating section 315 is configured to be operated by the user with a keyboard including cursor keys, numeric input keys, various types of function keys, and the like, a pointing device such as a mouse, a touch panel which is layered on the surface of the display section 314, or the like.

The operating section 315 outputs a control signal based on the operation which was made by the operator to the control section 311.

[2-2. Operation]

The control section 311 of the generator control console 31 which is configured in such a way includes the following function.

For example, the control section 311 has a function of setting the radiation irradiation conditions (tube voltage, tube current, irradiation time, and the like) in the radiation control section 111 on the basis of the operation made to the operating section 315 by the user.

The control section 311 has a function of outputting, to the radiation control device 11, the irradiation preparation signal and the irradiation instruction signal which were input from the switch 4.

The control section 311 has a function of obtaining information (for example, imaging conditions which are set, or the like) held by the detector control console 32 via the communicating section 312.

The control section 311 may have a function of outputting information (for example, radiation irradiation condition which is set in the control section 311 itself, or the like) held by the storage 313 via the communicating section 312.

[2-3. Imaging Preparation Processing]

The control section 311 includes a function of executing imaging preparation processing as shown in FIG. 6 or 7 when the dynamic imaging is set as an imaging mode which is one of the imaging conditions obtained from the detector control console 32.

(2-3-1. Obtaining Process)

In this imaging preparation processing, the control section 311 first executes an obtaining process (step S1).

In the obtaining process, the control section 311 obtains the length of the accumulation time from another device (for example, detector control console 32).

This "obtaining" includes receiving of a value transmitted from another device (for example, detector control console 32), directly inputting of a value to the generator control console 31 by the user, and the like.

The control section 311 in the present embodiment obtains the imaging conditions (imaging time, maximum imaging number, and frame rate) in addition to the accumulation time.

The control section 311 forms a setter by executing the process of step S1.

(2-3-2. Tube Current Calculation Process)

After the accumulation time is set, the control section 311 executes a tube current calculation process (step S2).

In the tube current calculation process, the control section 311 calculates such a proper range of the tube current that the start and end of the generation of one radiation pulse by the generator 1 are within one accumulation time when the imaging is performed with the accumulation time which was set in step S1.

The control section 311 in the present embodiment performs the calculation such that the upper limit value of the proper range is a fixed value and the lower limit value of the proper range is lower as the accumulation time is longer as shown in FIG. 8, for example.

By defining the start and end of generating the radiation pulse in such a way, the irradiation time of radiation becomes the time considering the inclination property of the radiation pulse.

The control section 311 forms a calculator by executing the process of step S2.

(2-3-3. Setting Process)

After the proper range of the tube current is calculated, the control section 311 executes a setting process.

In the setting process, the control section 311 sets the amount of the tube current.

When the setting process is executed, the control section 311 regulates setting of values out of the calculated proper range.

The way to set the amount of tube current is, for example, selection of an option or input of a numerical value.

When the amount of tube current is set by the selection of an option, as shown in FIG. 6, the control section 311 causes the display section 314 to display options of values within the proper range among the options of values which can be set as the amount of tube current (step S3), and the control section 311 sets, as the amount of tube current, the option of a value which was selected by the user from among the options displayed by the display section 314 (step S4).

Instead of displaying only the options of values within the proper range (not displaying the options of values out of the proper range), the regulation may be performed as in the following way, for example.

(A) gray down the options of the values out of the proper range (display options of values within the proper range by normal displaying)

(B) not receiving the selection operation performed to the options of the values out of the proper range (C) notify the error (that the input value is out of the proper range) when an option of the value out of the proper range is selected When the amount of tube current is to be set by the input of a numerical value, as shown in FIG. 7, the control section 311 receives the input of an arbitrary value by the user (step S5), and determines whether or not the arbitrary value which was input by the user is within the proper range (step S6). If the control section 311 determines that the input value is within the proper range (step S6; YES), the control section 311 sets the value which was input by the user as the amount of tube current (step S4A). On the other hand, if the control section 311 determines that the input value is out of the proper range (step S6; NO), the control section 311 notifies the error (step S7).

Instead of notifying the error, the regulation may be performed as in the following way, for example.

(a) request inputting a value again (b) stop the operation of at least one device forming the system 100

The above regulation methods are examples, and the regulation may be performed by using other methods.

The error may be notified by displaying characters or may be notified by sound.

The notification of error may be performed by the generator control console 31 itself, or the instruction to notify the error may be output to another device to cause the another device to perform the notification.

The control section 311 forms a setter, a regulator, and a notifier by performing the above controls.

The control section 311 in the present embodiment sets the tube voltage and the irradiation time.

The way to set the tube voltage and the irradiation time may be similar to the way to set the tube current or may be different from the way to set the tube current.

When the above-described imaging preparation processing is executed, the generator 1, the detector 2 and the additional device 5 come into a state able to perform the dynamic imaging (standby state of waiting for reception of the irradiation preparation signal and the irradiation instruction signal from the irradiation instruction switch).

Other devices (for example, detector control console 32) may include the function as the imaging control device.

The respective functions as the calculator, the setter, and the regulator may be dispersed in the system 100.

3. Effect

As described above, when imaging is performed with a set accumulation time, the system 100 in the present embodiment calculates such a proper range of the tube current that the start and end of generating one radiation pulse by the generator 1 are within one accumulation time, and regulates setting of values out of the calculated proper range. That is, the irradiation time of the radiation pulse is set to be a time considering the inclination property of the radiation pulse.

As a result, it is possible to generate the dynamic image which has no problem in quality even when the tube current is small.

4. Additional Techniques

Next, various techniques to be added to the above system 100 will be described.

The following various techniques can also be applied to radiation imaging systems (not having the functions as the calculator and the regulator) other than the above system 100.

[4-1. Additional Technique 1]

As shown in FIG. 9, the control section 311 may obtain the imaging conditions set in the detector control console 32 from the detector control console 32 (step S8), and determine whether the value of at least one of the accumulation time and the frame rate set in the generator 1 matches the value of the at least one of the accumulation time and the frame rate set in the detector 2 (step S9).

If the control section 311 determines that the value set in the generator 1 matches the value set in the detector 2 (step S9; YES), the control section 311 may output a permission to perform imaging to at least one of the generator 1 and the detector 2. If the control section 311 determines that the value set in the generator 1 does not match the value set in the detector 2 (step S9; NO), the control section 311 may output an instruction to notify the error (step S10).

The control section 311 may not output the permission to perform imaging but perform the process to be performed before imaging (for example, calculation of proper range).

By such a configuration, the control section 311 forms a determiner, and it is possible to prevent imaging from being performed in a state in which the imaging conditions set in the generator 1 and the detector 2 are different from each other.

[4-2. Additional Technique 2]

When imaging is performed to a site which does not easily transmit radiation or a subject which has a large body thickness, it is necessary to increase the tube voltage in order to shorten the wavelength of radiation.

When the change over time of the dose of radiation pulse is graphed, a nearly trapezoid is drawn with inclined rise and fall as mentioned above, and the inclinations of rise and fall (especially, fall) depend on not only the tube current but also the tube voltage. To be specific, as shown in FIG. 10, the inclination is steep when the tube current is small, but the inclination becomes more gradual as the tube voltage is larger. This is because more electric charges are supplied to the radiation source 12 (Q=CV) as the tube voltage is larger, and it takes time for the electric charges which were collected in the radiation source 12 to be taken away from the radiation source 12 after stop of the applying of the tube voltage.

Thus, in the above system 100, there is a possibility that when the dynamic imaging is performed by setting a large tube voltage, the timings to start and end the generation of radiation pulse cannot be within the accumulation time in the attempt to make the irradiation time of radiation pulse within the accumulation time, and the dynamic image influenced by that (failing to have the start and the end of generation of radiation pulse within the accumulation time) is generated.

Such a problem is more remarkable as the frame rate is higher.

After the process of step S1, as shown in FIG. 11, for example, the control section 311 may calculate the proper range of the value of at least one of the tube voltage and the irradiation time according to the length of the set accumulation time, in addition to the proper range of tube current (step S2A).

For example, as shown in FIG. 12, calculation is performed to have a fixed lower limit value of the proper range of each of the tube voltage and the irradiation time and to have the upper limit value of the proper range lowered as the accumulation time is shorter.

The control section 311 may regulate setting of the tube current out of the proper range and may regulate setting of the value of at least one of the tube voltage and the irradiation time out of the proper range (step S11).

The method to regulate the value setting may be similar to the method to regulate the value setting of the tube current mentioned above.

By such a configuration, it is possible to not only generate the dynamic image which has no problem in quality even when the tube current is small, but also generate the dynamic image which has no problem in quality even when the tube voltage is large.

As a result, it is possible to increase the site for which imaging can be performed, and it is possible to perform dynamic imaging of a subject which has a large body thickness.

[4-3. Additional Technique 3]

When a total dose of radiation emitted in one dynamic imaging is increased, there is a problem that the load on the generator 1 is increased and the life of generator 1 is shortened.

Thus, as shown in FIG. 13, for example, when a second value larger than a first value is set as a value of at least one of parameters among the tube current, the tube voltage and the irradiation time (only the irradiation time in FIG. 13), the control section 311 may lower the value(s) of parameter(s) which was not set to the second value among the tube current, the tube voltage and the irradiation time so that the total dose in one dynamic imaging does not exceed the total dose when the first value is set.

In this configuration, it is preferable to limit such that the total dose in a single imaging of the dynamic image is equal when the first value is set and when the second value is set (when the first value is n times the second value (n>1), set the value of other parameter(s) to 1/n).

By such a configuration, it is possible to prevent the lives of the generator 1 and the detector 2 from being shortened.

[4-4. Additional Technique 4]

When dynamic imaging is performed for the movement of a joint or the like, there may be a difference in imaging time among individuals depending on the treatment performed to the subject before the imaging (for example, reducing). Such a difference among individuals can be dealt with when the system 100 is made for long time dynamic imaging. However, the long time dynamic imaging has a larger exposure amount of the subject than the exposure amount of the short time dynamic imaging.

Thus, as shown in FIG. 14, for example, when a fourth value larger than a third value is set as a value of at least one of parameters among the maximum imaging time, the maximum imaging number and the dose of one radiation pulse (in FIG. 14, only the maximum imaging time), the control section 311 may lower the value(s) of parameter(s) for which the fourth value is not set among the maximum imaging time, the maximum imaging number and the dose of one radiation pulse so that the total dose in one dynamic imaging does not exceed the total dose when the third value is set.

In this configuration, it is preferable to limit such that the total dose in a single imaging of the dynamic image is equal when the third value is set and when the fourth value is set (to set other parameter(s) to 1/n when the third value is n times (n>1) the fourth value).

By such a configuration, even when the dynamic imaging is performed for a relatively long time, it is possible to suppress the exposure amount of the subject. As a result, it is possible to deal with imaging times which are different by the subject.

[4-5. Additional Technique 5]

In the dynamic imaging, it is necessary to change the frame rate when the dynamic imaging is performed, according to the site of interest, and how the site of interest moves and the speed of the movement.

On the other hand, even for a same site of interest, a different image quality is required for the dynamic image according to the purpose of diagnosis. For example, in the diagnosis of orthopedic field, a highly detailed dynamic image is required depending on the site of interest, while there are also sites of interest which do not require a high image quality. That is, not only the proper accumulation time and frame rate, but also the proper pixel pitch is necessary.

Thus, in the above system 100, as shown in FIG. 15, the binning number (frame rate/pixel pitch) to be set of the binning performed when the detector 2 reads out the signal value may be changed according to the set site of interest.

By such a configuration, it is possible to provide a highly detailed dynamic image as needed.

[4-6. Additional Technique 6]

When there are a plurality of generators 1, the property (actual irradiation time, tube voltage, tube current, total dose, and the like with respect to the set contents) is different by the generator 1 (manufacturer, and the like). Thus, when the generator 1 to be used is changed, there may be a difference in image quality of the obtained dynamic image even when the setting on the generator control console 31 is same.

Thus, in the above system 100, the connected generator 1 may be identified to adjust the proper range of the calculated value according to the identified generator 1.

The identifying of the generator 1 may be performed automatically by the system 100, or may be performed by a person who performs setup of the system 100 (serviceman of the manufacturer, or the like) performing a predetermined operation (selection of presetting).

By such a configuration, the control section 311 forms a device identifier, and it is possible to perform appropriate dynamic imaging even when the connected generator 1 is changed.

[4-7. Additional Technique 7]

As mentioned above, in the dynamic imaging, it is necessary to change the frame rate when the dynamic imaging is performed, according to the site of interest, and how the site of interest moves and the speed of the movement.

Thus, when the dynamic imaging is performed by setting the frame rate not considering the dynamic state speed, there is a possibility that the information necessary for diagnosis is not obtained from the obtained dynamic image and imaging needs to be performed again. The re-imaging leads to excessive exposure of the subject.

Thus, in the above system 100, the speed of a specific movement of the subject during imaging of the dynamic image may be detected so as to change the accumulation time and the frame rate to be set according to the detected speed.

The speed can be detected by the detector control console 32 obtaining a plurality of frames which were generated by the detector 2 and obtaining the difference in signal value between two frames, for example.

By such a configuration, the detector control console 32 forms a speed detector, and it is possible to have a proper dose of radiation according to the speed of specific movement of the subject.

[4-8. Additional Technique 8]

The point to focus on regarding the frame changes according to the test purpose (movement of the subject to be diagnosed). For example, the movement between consecutive frames may be diagnosed, or non-consecutive frames (for example, first and 100th frames) may be compared.

Figure 16A:
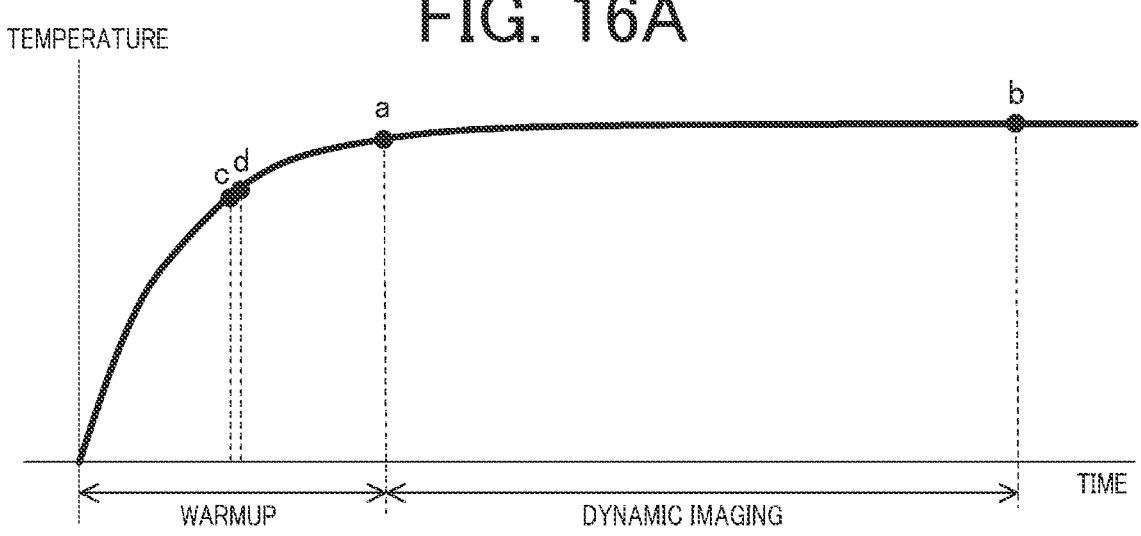
FIG. 16A and FIG. 16B are graphs each showing the change over time of the temperature of a reading section in the radiation detector in FIG. 3.

It is known that the detector 2 requires time to some extent until the temperature change of the reading section 23 causing heat noise is stabilized after the detector 2 is activated and starts warming up (operation of repeating the reading of signal value before starting the imaging of dynamic image), as shown in FIG. 16A.

When non-consecutive frames are compared, the difference in heat noise is large. Thus, it is necessary to compare frames (for example, the frames generated at the timings a and b in FIG. 16A) which were generated after the temperature change of the reading section 23 stabilizes. On the other hand, when the movement between consecutive frames is diagnosed, the difference in heat noise between the frames is small. Thus, the influence on diagnosis is small even when the comparison is made between the frames (for example, the frames generated at the timings c and d in FIG. 16A) which were generated before the temperature change of the reading section 23 stabilizes. It is a waste of time to wait until the temperature change of the reading section 23 stabilizes to perform imaging in such a situation (that is, when the movement between consecutive frames is diagnosed).

Thus, in the above system 100, the console 3 may set a test purpose and set the length of warmup period according to the test purpose which was set.

Figure 16B:
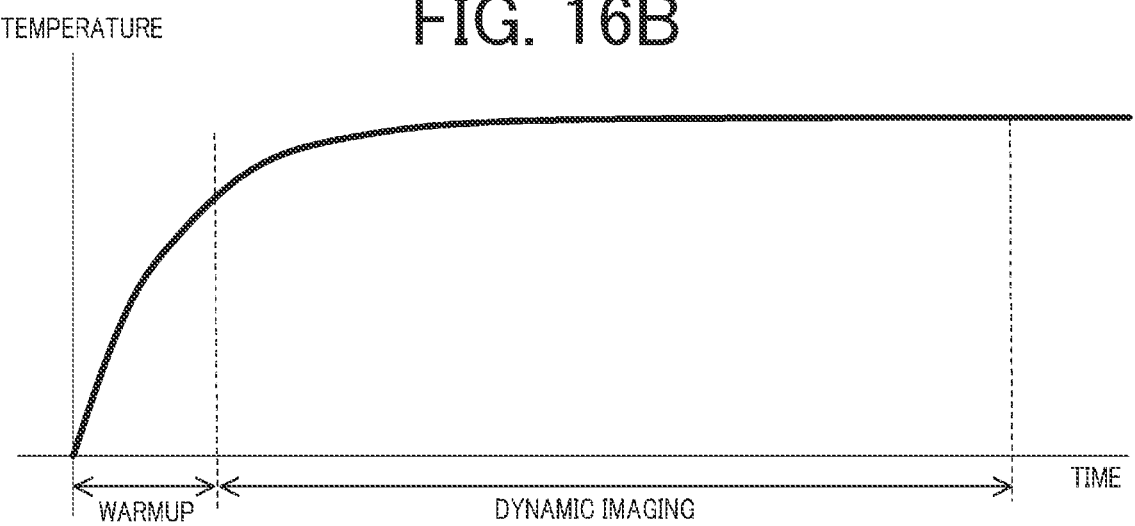

To be specific, when consecutive frames are compared, as shown in FIG. 16B, the warmup period is shortened.

By such a configuration, it is possible to set the warmup period of a proper length according to the test purpose, and raise the efficiency of dynamic imaging.

[4-9. Additional Technique 9]

In the dynamic imaging, there may occur the phenomenon called lag in which the electric charges when generating a frame (referred to as a previous frame) influence the following frame. This lag mostly occurs in the form of superposing the image shadow of the previous frame on the following frame as shown in FIG. 17.

One of the causes of the lag is a component (long time constant lag) which attenuates with a relatively long time constant (approximately several seconds) after reception of radiation irradiation.

Figure 18A:
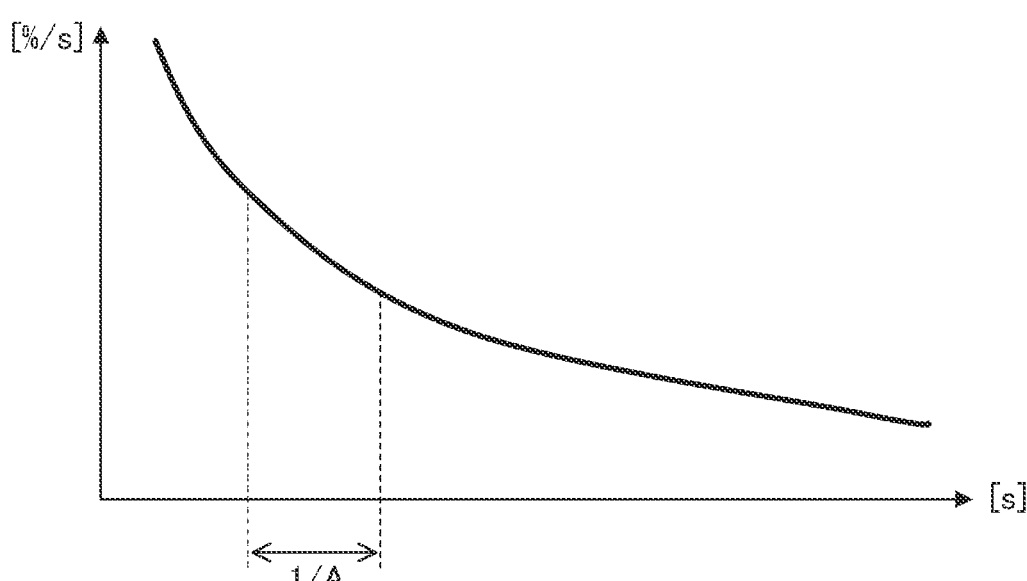
FIG. 18A and FIG. 18B are graphs each showing the change over time of a long time constant lag.
Figure 18B:
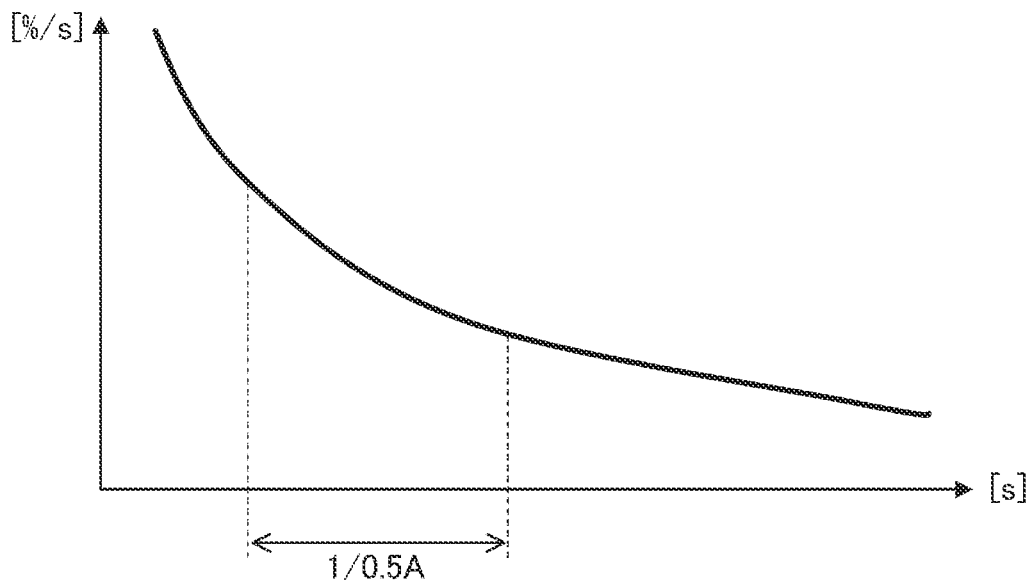

The long time constant lag can be removed by performing the weighted difference processing using the previous frame to the target frame. However, since the long time constant lag is a function which depends on time, the generation amount is larger as the frame rate is smaller (integration time is longer) as shown in FIG. 18A and FIG. 18B.

Thus, in the above system 100, the weighting coefficient of the lag correction processing may be switched according to the set frame rate.

By such a configuration, it is possible to appropriately correct the lag which is different in the degree of generation according to the frame rate of the imaging.

The lag correction has a demerit of increasing the image noise due to the difference processing. The lag has a property that the visibility is high in imaging of the lateral face of a body trunk which is imaging with a thick subject and with a large difference in signal value between the direct transmitting region and the site of interest, and that the visibility is low in imaging of a thin subject such as limbs.

Thus, it is desirable to perform the lag correction to only the imaging which requires correction.

Accordingly, the on/off may be switched for even the same frame rate when the lag is not a problem clinically by the imaging site, positioning and the site of interest.

[4-10. Additional Technique 10]

In order to improve granularity of the dynamic image and reduce the lateral noise, inter-frame image correction processing (for example, recursive filter) can be performed to each frame.

However, when the dynamic imaging is performed by changing the frame rate and/or the imaging site (speed of movement) and the same inter-frame image processing is performed to the generated dynamic image, the artifact may occur due to the processing.

Thus, in the above system 100, the coefficient of the recursive filter may be switched according to the set frame rate and/or imaging site.

By such a configuration, even when the dynamic imaging is performed by changing the frame rate and/or the imaging site, it is possible to improve the image quality while preventing the generation of artifact in the dynamic image.

[4-11. Additional Technique 11]

The wireless communication may lack in stability compared to the wired communication. Thus, it may take time to transfer the data of the dynamic image from the detector 2 to the console 3, or the transferring may be impossible.

When the data transferring is delayed, the image confirmation regarding whether or not the reimaging performed after the imaging is necessary is delayed. Thus, the subject needs to wait for a long time, and the burden on the subject is increased.

Thus, when the communication between the detector 2 and the console 3 is performed wirelessly in the above system 100, setting of a frame rate which is relatively high may be regulated to reduce the data amount to be transferred.

The frame rate with which the data of dynamic image can be transmitted without delay even by the wireless communication may be calculated on the basis of the current communication state (such as actual throughput when the communication is actually performed) and the calculated frame rate may be notified.

When the delay and the like cannot be resolved by changing the frame rate as a result of the calculation of frame rate, the notification urging the wired imaging may be performed.

By such a configuration, it is possible to surely transfer the data of dynamic image in a short time even by the wireless communication.

[4-12. Additional Technique 12]

When the processing performance of devices forming the system 100 is not sufficient (for example, the console or the like mounted on the visiting car for a doctor's round often has a low processing performance compared to the processing performance of a console or the like set in the imaging room), it may take time to transfer the data of dynamic image of a high frame rate from the detector 2 to the console 3 or to perform image processing to the dynamic image in the detector 2 and the console 3.

When the transfer of data and the image processing are delayed, the image confirmation regarding whether or not the reimaging performed after imaging is necessary is delayed. Thus, the subject needs to wait for a long time, and the burden on the subject is increased.

Thus, in the above system 100, at least one of the upper limit and the lower limit of the frame rate when the dynamic imaging is performed may be calculated according to the processing performance of the console 3 (core number of the control section 311, memory capacity, or the like) and setting of frame rates out of the calculated range may be regulated.

By such a configuration, it is possible to finish the work from the dynamic imaging to the image confirmation in a short time irrespective of the imaging environment (for example, the processing performance of device which is different between doctor's round and general imaging).

[4-13. Additional Technique 13]

The maximum imaging number of the dynamic image greatly depends on the memory capacity of the detector 2. Thus, in the above system 100, the dynamic imaging at the set frame rate cannot be performed depending on the memory in the detector 2.

Thus, in the above system 100, the imaging time and the frame rate may be determined according to the memory capacity of the detector 2.

By such a configuration, it is possible to perform dynamic imaging appropriate for the connected detector 2.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiation imaging system comprising:
   a radiation generator that includes a radiation source which generates a radiation pulse;
   a radiation detector that includes a plurality of charge accumulators for accumulating and releasing electric charges to be read out as signal values according to received radiation and that generates a dynamic image formed of a plurality of frames; and
   a hardware processor that:
   controls the radiation generator;
   identifies the radiation generator;
   calculates an allowable range of at least one of an irradiation time, a tube voltage, a tube current or a total dose according to a length of an accumulation time for which the plurality of charge accumulators are allowed to accumulate electric charges and in accordance with the identified radiation generator; and
   regulates setting of a value out of the calculated allowable range.

2. The radiation imaging system according to claim 1, wherein a radiation generator to be used is switchable among the plurality of radiation generators.

3. The radiation imaging system according to claim 1, wherein the hardware processor:
   identifies the radiation generator;
   calculates an allowable range of a frame rate according to the identified radiation generator; and
   sets the frame rate according to at least one of a site of interest or an imaging application.

4. The radiation imaging system according to claim 1, wherein the hardware processor sets at least one of a weighting coefficient of the lag correction processing or a coefficient of a recursive filter in accordance with a frame rate.

5. The radiation imaging system according to claim 3, wherein the hardware processor sets at least one of a weighting coefficient of the lag correction processing or a coefficient of a recursive filter in accordance with the set frame rate.

6. The radiation imaging system according to claim 1, wherein the hardware processor:
   identifies the radiation generator; and
   according to the identified radiation generator,
   calculates the allowable range; and
   displays options or receives an input of a value.

7. The radiation imaging system according to claim 6, wherein the hardware processor:
   receives the input of the value;
   determines whether or not the input value is within the allowable range; and
   in response to the input value being out of the allowable range, performs a regulation or notifies an error.

* * * * *